United States Patent [19]

Sasaki et al.

[11] Patent Number: 4,995,871
[45] Date of Patent: Feb. 26, 1991

[54] NEEDLE DETACHER FOR SYRINGE

[75] Inventors: Hirotaka Sasaki, Sayama; Aguri Tanaka, Tokyo; Hiroyuki Inagaki, Kamakura; Tatsuo Suzuki, Tokyo; Kenji Asakura, Funabashi, all of Japan

[73] Assignee: Snow Brand Milk Products Co., Ltd., Hikkaido, Japan

[21] Appl. No.: 303,228

[22] Filed: Jan. 30, 1989

[30] Foreign Application Priority Data

Feb. 4, 1988 [JP] Japan .............................. 63-14177[U]
Nov. 16, 1988 [JP] Japan ........................... 63-149247[U]

[51] Int. Cl.⁵ ...................... A61M 5/00; B65D 83/10
[52] U.S. Cl. ................................. 604/110; 604/192;
206/366; 220/346; 220/348
[58] Field of Search ................. 604/110, 192, 263;
206/366, 365, 364, 63.5; 220/345, 346, 348, 254

[56] References Cited

U.S. PATENT DOCUMENTS

| | | | |
|---|---|---|---|
| 3,792,803 | 2/1974 | Kessler | 222/511 |
| 4,494,652 | 1/1985 | Nelson et al. | 206/366 |
| 4,667,821 | 8/1987 | Shillington | 206/366 |
| 4,738,362 | 4/1988 | Burns et al. | 206/366 |
| 4,798,587 | 1/1989 | Willoughby | 604/110 |
| 4,801,013 | 1/1989 | Bruno | 206/366 |
| 4,862,573 | 9/1989 | Kelson et al. | 29/240 |
| 4,867,309 | 9/1989 | Germain | 266/366 |
| 4,922,597 | 5/1990 | Ikeda et al. | 29/240 |
| 4,940,157 | 7/1990 | Inagaki | 220/254 |
| 4,955,865 | 9/1990 | Steiner et al. | 604/192 |

FOREIGN PATENT DOCUMENTS

| | | |
|---|---|---|
| 80882 | 6/1983 | European Pat. Off. |
| 2601512 | 3/1977 | Fed. Rep. of Germany ...... 604/110 |
| 88/00067 | 1/1988 | World Int. Prop. O. |
| 8806133 | 8/1988 | World Int. Prop. O. |

Primary Examiner—C. Fred Rosenbaum
Assistant Examiner—Mark O. Polutta
Attorney, Agent, or Firm—Griffin, Branigan & Butler

[57] ABSTRACT

Here is disclosed a needle detacher for syringe adapted to detach a needle after use for injection or blood-collecting from the associated syringe cylinder for easy and safe disposal, comprising a container main body, a lid assemble consisting of inner and outer lids, a needle chute opening formed through the outer lid, and a needle trap opening defined by the inner and outer lids so that a syringe cylinder or the outer lid may be forcibly rotated with the needle neck being held in the needle trap opening to detach the needle from the syringe cylinder and then the needle may be received through the needle chute opening into the container main body, wherein the needle chute opening is adapted to be closed by the inner lid which is slidable with respect to the outer lid so that the needle neck can be held by the inner lid cooperating with the outer lid.

14 Claims, 9 Drawing Sheets

NEEDLE DETACHER FOR SYRINGE

BACKGROUND OF THE INVENTION

The present invention relates to a needle detacher for syringe improved to be easily manipulated without causing any infections accident.

Recently the disposable syringe has come into wide use for injection or blood-collecting.

Such syringe is usually made of plastic from a hygienic viewpoint, i.e., so that it may be disposable after use to avoid not only any possible infectious accident but also to eliminate conventional requirement for rather troublesome procedure of sterilization.

Once a syringe has been used for injection or blood-collecting, the needle is detached from the cylinder of this syringe and subjected to disposal at an appointed place.

More specifically, the needle put on the syringe cylinder is loaded into a needle cover, then the needle is detached together with the needle cover from the syringe cylinder and thrown away at the appointed place.

According to such method, it is rather difficult to load the needle into the needle cover since the latter has a relatively small mouth and sometimes the needle point pierces the fingers holding the needle cover. This may cause an infectious accident, should the needle be a contaminated needle which has been used for a patient having pathogenic bacteria or viruses.

To overcome such problem, the inventors have previously proposed the needle detacher to be used without a danger of infectious accident in Japanese Utility Model Application No. 1987-11852.

FIG. 21 of the accompanying drawing illustrates the invention disclosed in said Japanese Utility Model Application. Referring to this figure, reference numeral 41 designates a main body of a needle receiving container having its upper side fully opened. An outer lid 42 is secured to the container main body 41 and an inner lid 43 is slidably incorporated in the outer lid 42.

The outer lid 42 has a needle trap opening 45 comprising a rectangular opening 45a adapted to be engaged with a needle neck 47 and a fan-shaped opening 45b which is continuous with said rectangular opening 45a and functions as a needle chute opening.

Reference numeral 46 designates a syringe cylinder on which the needle neck 47 is fit. The needle neck 47, as being put on the syringe cylinder 46, is inserted into the fan-shaped opening 45b, then moved into engagement with the rectangular opening 45a and held therein. From such condition, the syringe cylinder 46 or the container main body 41 is rotated until the needle 48 is detached from the syringe cylinder 46 and then the needle 48 falls through the needle chute openings 45b into the container main body 41.

Before the container is thrown away together with the needles contained therein, the needle trap opening 45 of the outer lid 42 must be covered with the inner lid 43.

With the needle detacher as has been mentioned above, however, detachment of the needle neck 47 from the syringe cylinder 46 can not be smoothly achieved, since the needle neck 47 is held only by the rectangular opening 45a of the needle trap opening 45 with an unadequate holding effect. Furthermore, the inner lid 43 may be unintentionally rotated during transport of the container so as to expose the fan-shaped opening 45b of the needle trap opening 45 and, as a result, one or more needles may be exposed to the exterior, since the inner lid 43 is rotatably mounted. The needle thus exposed to the exterior may cause an injury. In addition, the inner lid 43 requires manual operation which is troublesome for the user.

Finally, a dimension of the fan-shaped opening 45b is relatively small, so it is impossible to protect the user perfectly against a danger that the needle point might pierce the fingers holding the container main body 41 during insertion of the needle neck 47 put on the syringe cylinder 46 into the needle trap opening 45. Consequently, there still remains a danger that the needle might cause an infectious accident if the needle has been contaminated with pathogenic bacteria or viruses.

SUMMARY OF THE INVENTION

In view of the problems encountered by the needle detacher of prior art, a principal object of the present invention is to provide an improved needle detacher for syringe adapted to be easily manipulated without causing any infectious accident.

According to the present invention, the above-mentioned object is achieved by a needle detacher for syringe comprising a container main body, a lid assembly consisting of inner and outer lids, a needle chute opening formed through said outer lids, and a needle trap opening defined by said inner and outer lids so that a syringe cylinder or the outer lid may be forcibly rotated with the needle neck being held in said needle trap opening to detach the needle from the syringe cylinder and then the needle may be received through the needle chute opening into the container main body, wherein said needle chute opening is adapted to be closed by said inner lid which is slidable with respect to said outer lid so that the needle neck can be held by said inner lid cooperating with said outer lid.

There is provided a spring between the inner and outer lids so that the inner lid may expose the needle trap opening immediately after the needle has been detached from the syringe cylinder and there is provided stop means for the inner lid by which the inner lid may be maintained in its closed position against the action of said spring.

It is also contemplated that the stop means for the inner lid is adapted to be reversible so as to stop or release a rear end of the inner lid or that a foldable band provided on the inner lid is adapted to be anchored on a pin projecting from the outer lid, if necessary.

It is further contemplated that there is provided a spring adapted to thrust the needle neck from the needle trap opening towards the needle chute opening as the inner lid is retracted from a position at which said inner lid holds said needle neck in cooperation with the outer lid or that said needle neck is thrusted by a wall edge of a top plate.

It is still further contemplated that a protective cover radially extends from a periphery of the outer lid to protect the fingers against the needle point during insertion of the needle neck into the needle trap opening.

With the needle detacher for syringe of the present invention, the inner lid which has covered the needle chute opening is now retracted under the action of the spring incorporated in said inner lid upon release of the stop means and thereby exposes the needle trap opening into which the needle neck is inserted. During insertion of the needle neck into the needle trap opening, the protective cover radially extending from the periphery of this outer lid protects the user's finger. In this way, there is no danger that the needle point might pierce the user's finger and cause an infectious accident even if the needle point has been contaminated with pathogenic bacteria or viruses. Then, the inner lid is pushed towards the needle trap opening with the hand holding the container main body against the force of said spring so as to hold the needle neck firmly by the inner lid cooperating with the outer lid. The syringe cylinder is rotated with the other hand relative to the needle neck held by the inner and outer lids, and thereby the needle neck is detached from the syringe cylinder. Upon release of a hold on the inner lid after detachment of the needle neck from the syringe cylinder, the inner lid is retracted under the action of said spring to expose the needle trap opening again and the needle neck is thrusted out from the needle trap opening under the action of the spring associated with said needle trap opening or under the action of the top plate wall edge towards the needle chute opening. In this manner, the needle neck can be so firmly held by the inner lid cooperating with the outer lid that detachment of the needle can be stably and smoothly accomplished. Additionally, manipulation of the inner lid is not troublesome because the inner lid is retracted under the action of the spring merely by pushing the inner lid with the hand holding the container and then loosing the hold thereon.

After a plurality of the needles have been received in the container, the inner lid is pushed forward, then the rear end thereof is stopped by the stop means so that the inner lid is maintained to cover the needle chute opening, and the entire needle detacher containing the plurality of needles therein is thrown away. Thus, sealing of the container main body is surely maintained only by the stop means for the inner lid and thereby the danger is effectively avoided that the needles contained within the container main body might be exposed to the exterior or discharged therefrom and cause an injury during transport of the container.

DETAILED DESCRIPTION OF THE INVENTION

Figure 1:
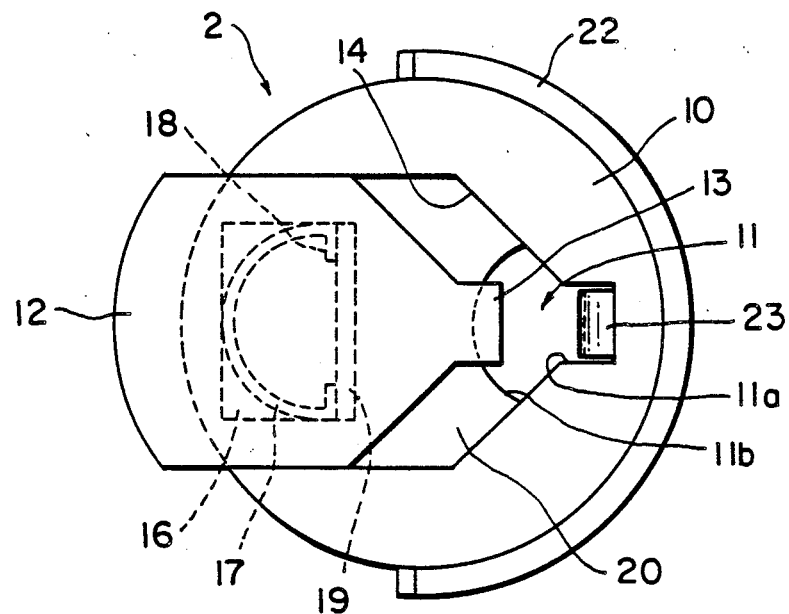
FIG. 1 is a plan view of an inner lid.
Figure 2A:
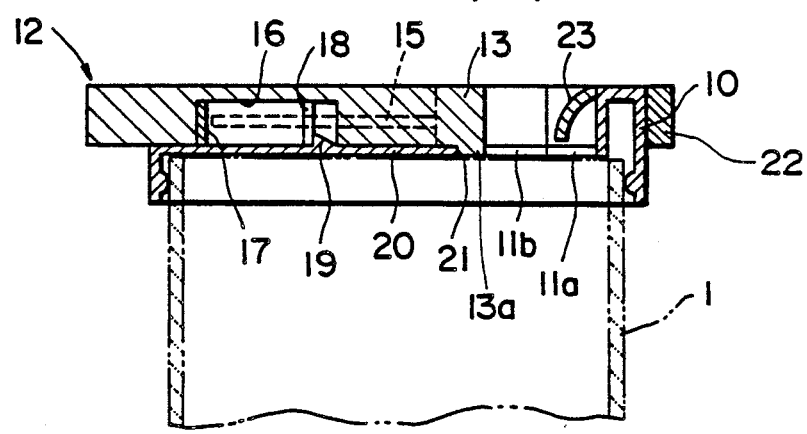
FIG. 2(A) is a sectional view of said inner lid and FIGS. 2(B), (C) and (D) illustrate selectively useful spring shapes.
Figure 2B:
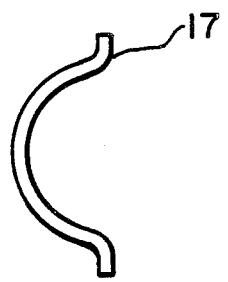
Figure 2C:
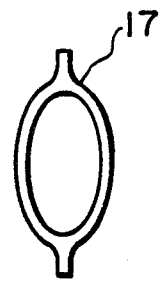
Figure 2D:
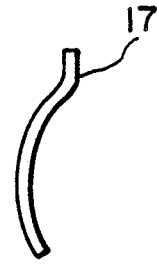
Figure 3:
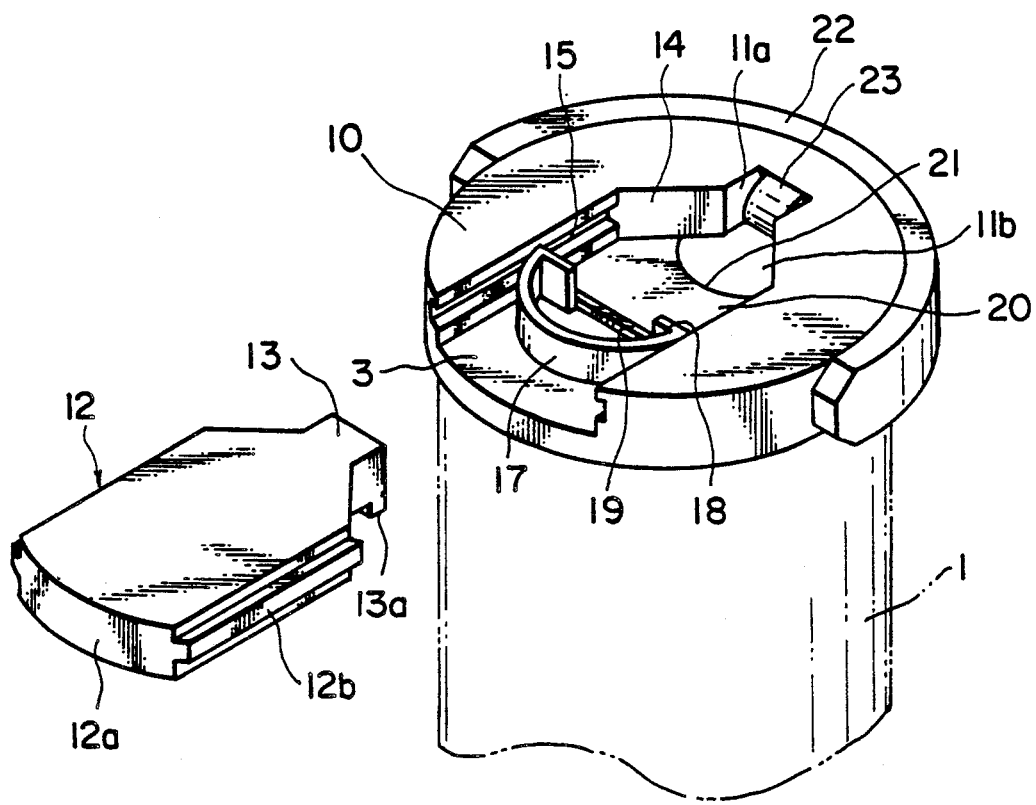
FIG. 3 is a perspective view of an outer lid.

The invention will be described in reference with respective embodiments thereof. FIGS. 1, 2 and 3 illustrate a first embodiment of the present invention, in accordance with which a lid assembly 2 comprising an outer lid 10 and an inner lid 12 is secured to the top of a container main body 1. The outer lid 10 includes a notch 3 having shape and dimension corresponding to those of the inner lid 12. The notch 3 is surrounded by a wall portions 14 and overlies a top plate 20. There is provided beneath a forward end of the notch 3 a needle trap opening 11 consisting of a rectangular opening 11a and a needle chute opening 11b being continuous with said rectangular opening 11a. The inner lid 12 is substatially pentagonal but has an arc-shaped rear surface 12a and is provided on its forward end with a projection 13 adapted to be engagedc into the rectangular opening 11a.

The inner lid 12 is slidable with respect to the outer lid 10. Specifically, there are provided in the wall portions 14 extending along opposite sides of the notch 3 formed in the outer lid 10 with grooves 15 while there are provided on opposite sides of the inner lid 12 with ridges 12b adapted to be slidably engaged into the corresponding grooves 15.

There is provided in the underside of the inner lid 12 with a cavity 16 to accomodate a bow-shaped spring 17 having an intermediate portion bearing against a rear wall of said cavity 16 and opposite ends 18 bearing against a spring shoe 19 projecting from the top plate 20 of the outer lid 10.

With a consequence, the inner lid 12 is radially biased to be disengaged from the outer lid 10.

Shape of the spring 17 is not limited to said bow-shape but may be coil-shaped, ring-shaped, or cantilever-shaped.

Said projection 13 of the inner lid 12 includes a ridge 13a downwardly projecting from the underside thereof. This ridge 13a is adapted to be engaged with a wall end 21 of the top plate 20 and thereby to function as stop means for the inner lid 12 against the action of the spring 17 associated with said inner lid 12. The projection 13 is thereby prevented from retracting beyond the needle chute opening 11b of the needle trap opening 11.

The rectangular opening 11a is incorporated with a spring 23 functioning to thrust the needle neck towards the needle chute opening 11b.

A semicircular band 22 is pivotally mounted so as to be normally engaged with the outer periphery of the outer lid 10 substantially along one half thereof. This may be pivotally reversed to bear against the rear surface 12a of the inner lid 12 and thereby to engage the projection 13 of the inner lid 12 into the rectangular opening 11a against the action of the spring 17 so that the needle trap opening 11 may be fully covered with the inner lid 12.

Figure 4:
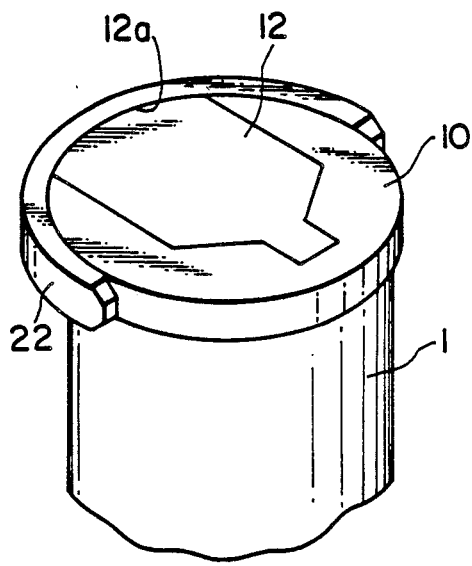
FIGS. 4 through 7 are perspective views successivley illustrating how a needle detacher constructed as a first embodiment of the present invention is manipulated.

Now a manner in which the first embodiment of the present invention is used will be discussed in reference with FIGS. 4 through 7. As shown in FIG. 4, the band 22 is brought in to engagement with the rear surface 12a of the inner lid 12 to retain the latter at a position fully covering the needle trap opening 11 and thereby to maintain the container in its sealed condition.

Figure 5:
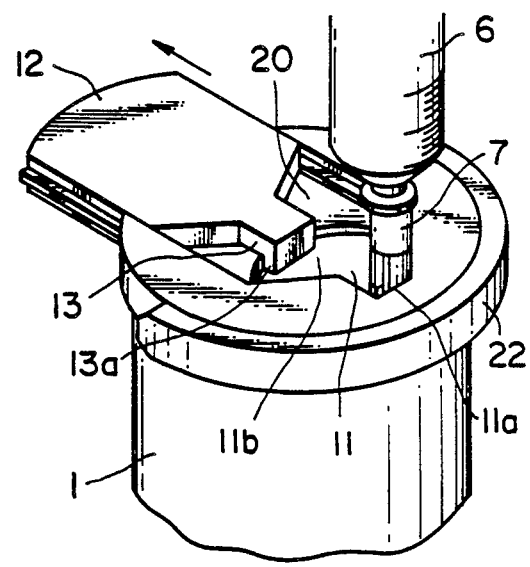

Upon a pivotal movement of the hand 22 to a position as shown in FIG. 5, the inner lid 12 is moved in a direction as indicated by an arrow under the biasing effect of the spring 17 to uncover the needle trap opening 11.

With the needle trap opening 11 thus uncovered, a needle neck 7 of the syringe is inserted first into the needle chute opening 11b and then horizontally moved into the rectangular opening 11a, as shown by FIG. 5.

Figure 6:
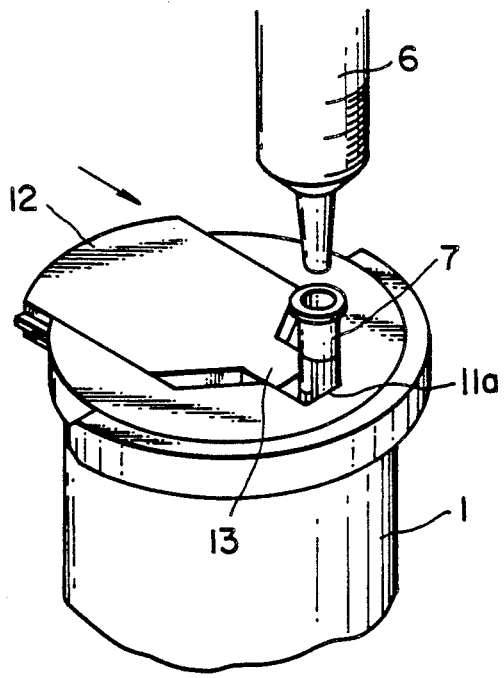

After the needle neck 7 has been inserted into the rectangular opening 11a, the inner lid 12 may be manually pushed in a direction as indicated by an arrow in FIG. 6 to hold the needle neck 7 firmly by the projection 13 cooperating with the rectangular opening 11a and the syringe cylinder 6 may be forcibly rotated with respect to the needle neck thus firmly held to detach the needle neck 7 from thhe syringe cylinder 6.

Figure 7:
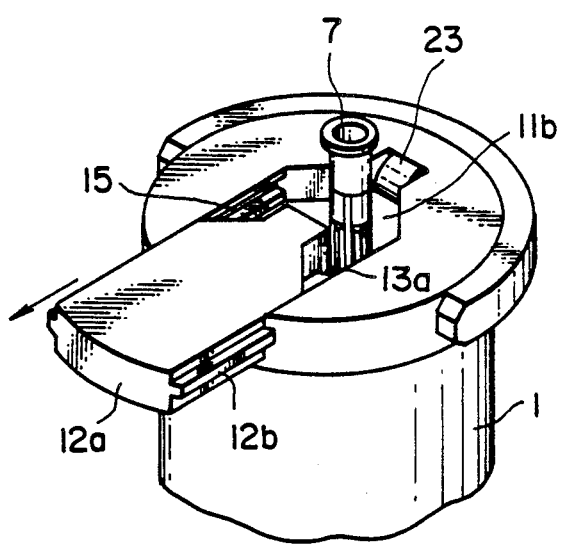

By loosing a hold on the inner lid 12, the latter is allowed to be moved under the action of the spring 17 in a direction as indicated by an arrow in FIG. 7 and simultaneously the needle 8 is thrust out from the rectagular opening 11a under the action of the spring 23 provided in the rectangular opening 11a towards the needle opening 11b through which said needle 8 falls into the container main body 1.

When the number of the needles has adequately increased, the band 22 is pivotally moved back to a position as shown in FIG. 4 to lock the inner lid 12 and thereby to maintain the container sealed before disposed thereof.

FIGS. 8 through 13 illustrate the second embodiment of the present invention. The rectangular opening 11a forming a part of the needle trap opening 11 in the first embodiment of the present invention is formed through a head of the inner lid 12 in this embodiment so that the inner lid 12 is retracted under the action of the spring 17 together with the needle neck 7 held in the rectangular opening 12c until the needle neck 7 bears against the wall end 21 of the top plate 20 and, as a result, the needle neck 7 is thrust out from the rectangular opening 12c towards the needle chute opening 11b through which said needle neck 7 falls into the container main body 1.

According to this embodiment, there is provided a foldable band 24 used to cover the needle chute opening 11b. Normally, the foldable band 24 is anchored with an anchoring hole 24a being put on a pin 25 projecting from the inner lid 12 so that the band 24 is accommodated in a groove 28 of the inner lid 12 and thereby the rectangular opening 11a is uncovered. To close the needle chute opening 11b, the inner lid 12 is pushed forward, then the band 24 is folded forward and anchored with the anchoring hole 24a being put on a pin 26 projecting from the notch 27 which is provided on a forward portion of the outer lid 10 at a position symmetrically opposed to the pin 25 projecting from the inner lid 12 so as to close the needle chute opening 11b.

Now, a manner in which the second embodiment of the present invention is used will be explained in reference with FIGS. 8 through 13.

Figure 8:
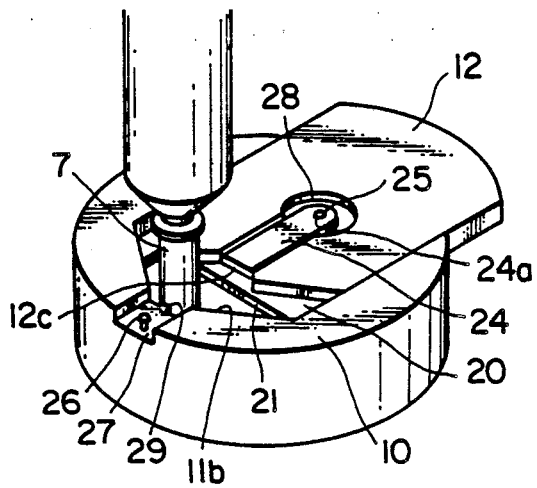
FIGS. 8 through 13 are perspective views successively illustrating how a needle detacher constructed as a second embodiment of the present invention is manipulated.
Figure 9:
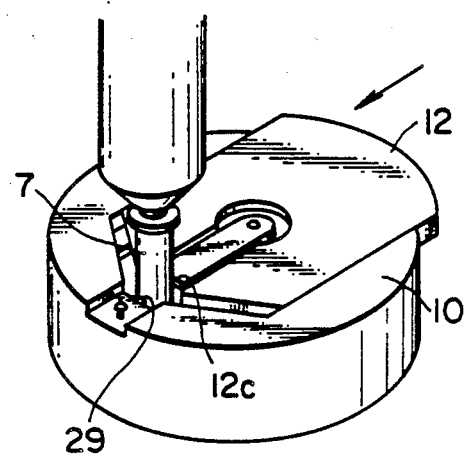

FIG. 8 illustrates a situation in which the inner lid 12 has been retracted to uncover the needle chute opening 11b and the needle neck 7 of the syringe has been inserted into said opening 11b and FIG. 9 illustrates a situation in which the inner lid 12 has been pushed forward to hold the needle neck 7 by the rectangular opening 12c cooperating with a projection 29 of the outer lid 10.

Figure 10:
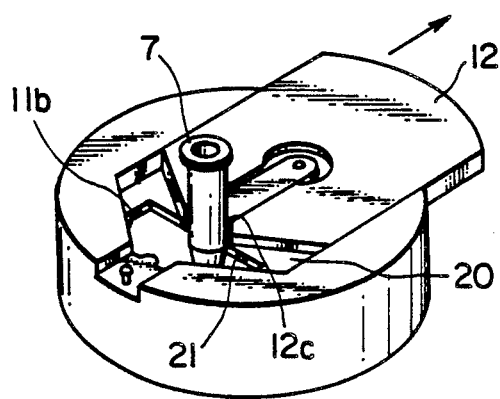
Figure 11:
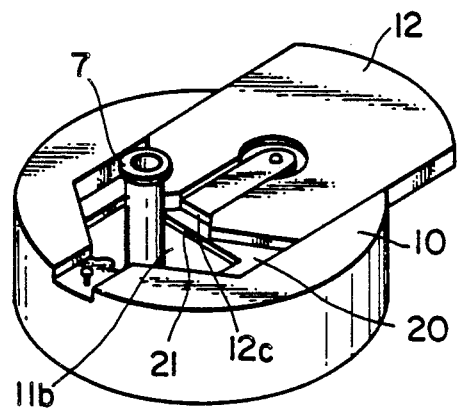
Figure 12:
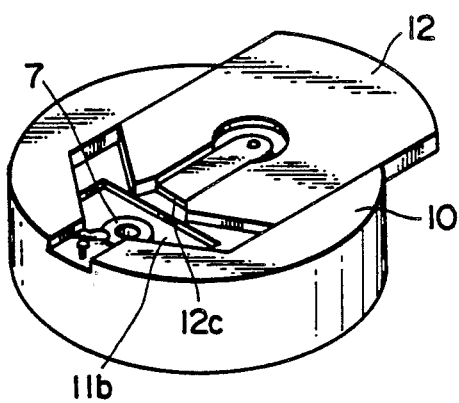

FIGS. 10, 11 and 12 successively illustrate a process in which the inner lid 12 is retracted together with the needle neck 7 which has been detached from the syringe cylinder 6 and then held in the rectangular opening 12c until the needle neck 7 bears against the wall end 21 of the top plate 20 and, as a result, the needle neck 7 is thrusted out from the rectangular opening 12c towards the needle chute opening 11b through which the needle neck 7 falls into the container main body 1.

As in the first embodiment, the present embodiment permits the needle chute opening 11b to be covered with the inner lid 12 and additionally permits also the needle neck 7 to be held by the rectangular opening 12c cooperating with the projection 29.

Figure 13:
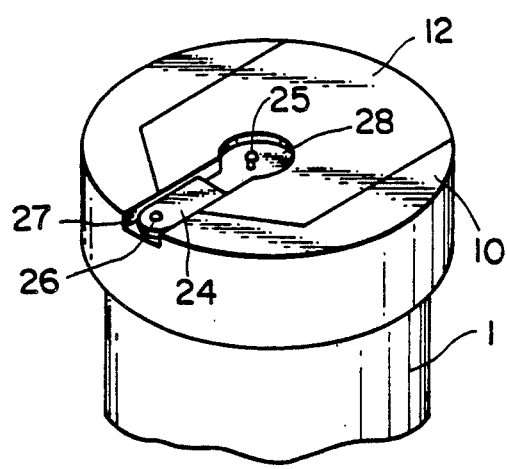

FIG. 13 illustrates a situation in which the inner lid 12 has been pushed forward and the band 24 has been anchored with the anchoring hole 24a being put on the pin 26 projecting from the bottom of the groove 27 so as to cover the needle chute opening 11b with the inner lid 12.

In this manner, it is assured that the needles contained within the container main body 1 are prevented from being unintentionally exposed to the exterior or being discharged therefrom. Also in this embodiment, the wall end 21 of the top plate 20 is designed so that the needle neck 7 bears against the wall end 21 before the inner lid 12 has been retracted and then stopped by the stop means.

FIGS. 14 through 18 illustrate the third embodiment of the present invention, in accordance with which a recess 30 formed in the forward end of the inner lid 12 cooperating with a recess 31 formed in the outer lid 10 to hold the needle neck 7 therebetween.

These recesses 30, 31 have their inner walls formed as saw teeth to assure that the needle neck 7 should be unrotatably held therebetween.

The present embodiment is identical to the second embodiment in that the needle neck 7 bears against the wall end 21 of the top plate 20 before the inner lid 12 has been retracted and then stopped by the stop means. More specifically, the inner lid 12 is retracted under the action of the spring 17 together with the needle neck 7 held in the recess 30 thereof and, during this backward movement of the inner lid 12, the needle neck 7 bears against the wall end 21 of the top plate 20. The needle neck 7 is thereby thrusted out from the recess 30 so as to fall into the container main body 1.

Figure 14:
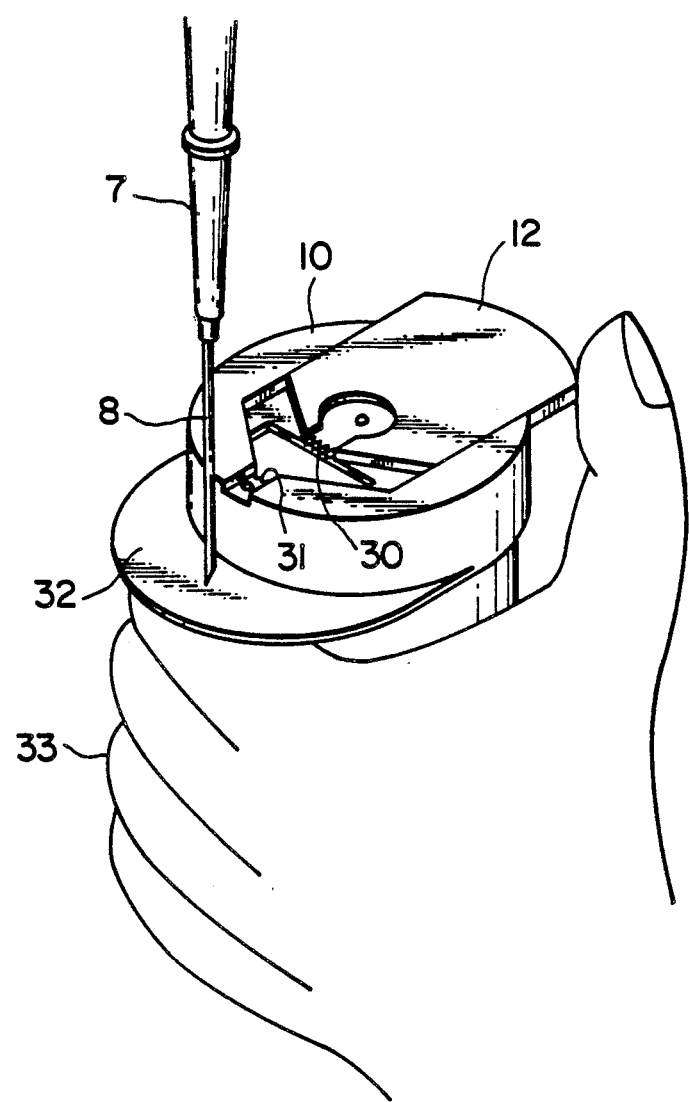
FIGS. 14 through 18 are perspective views successively illustrating how a needle detacher constructed as a third embodiment of the present invention is manipulated.

As will be apparent from FIG. 14, the outer lid 10 is provided along a part of its outer periphery with a protective cover 32 to prevent the needle 8 from accidentally piercing the user's finger 33 during insertion of the needle neck 7 into the needle trap opening 11.

Figure 15:
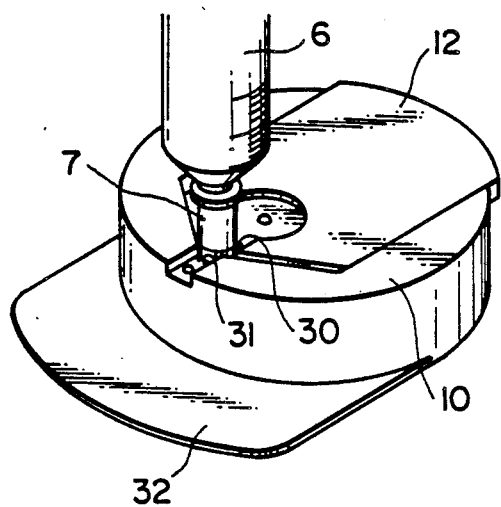
Figure 16:
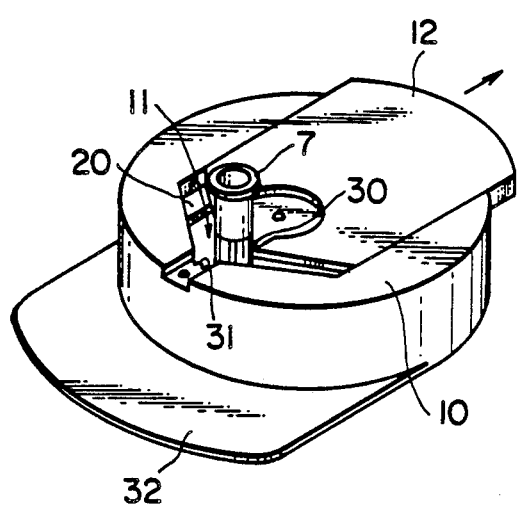
Figure 17:
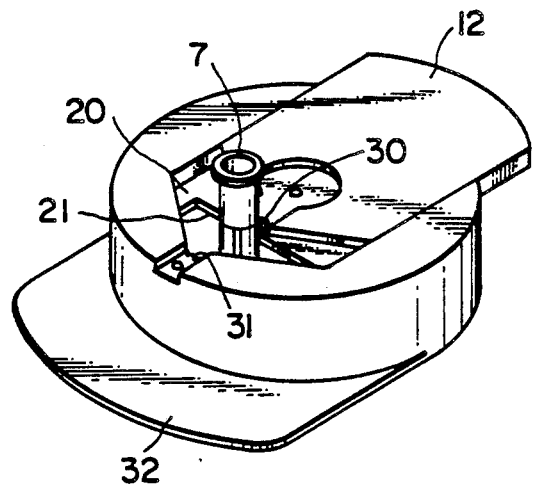
Figure 18:
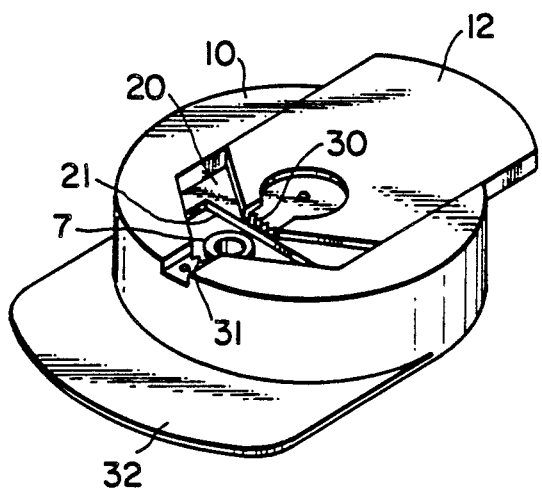

A manner in which the third embodiment of the present invention is used will be described in reference with FIGS. 15 through 18. FIG. 15 illustrates a situation in which the needle neck 7 is held between the recess 30 formed in the inner lid 12 and the recess 31 formed in the outer lid 10, and FIGS. 16 through 18 successively illustrate a process in which the inner lid 12 is retracted together with the needle neck 7 which has been detached from the syringe cylinder and then held by the recess 30 formed in the forward end of said inner lid 12 and, during this backward movement of the inner lid 12, the needle neck 7 bears against the wall end 21 of the top plate 20. The needle neck 7 is thereby thrusted out from the recess 30 so as to fall into the container main body 1.

As in the first and second embodiments, the present embodiment not only permits the needle trap opening 11 to be covered with the inner lid 12 but also permits the needle neck 7 to be firmly held by the recess 30 of the inner lid 12 cooperating with the recess 31 of the outer lid 10.

To seal the container main body 1, the semicircular band 22 adapted to be engaged around the outer lid 10 substantially along one half of the outer periphery thereof is pivotally mounted on the outer lid 10 and the inner lid 12 is locked by this band 22. Alternatively, the inner lid 12 is provided with the foldable band 24 which is adapted to be anchored on the pin 26 projecting from the outer lid 10.

The band 22 may be configured to serve also as the protective cover 32. However, if the band 22 is excessively enlarged thereby, such band 22 might be caught and taken off from its effective position by any adjacent obstacles during transport of the container. To avoid such a danger, it is preferable that the band 22 and the protective cover 32 are separately provided.

Figure 19:
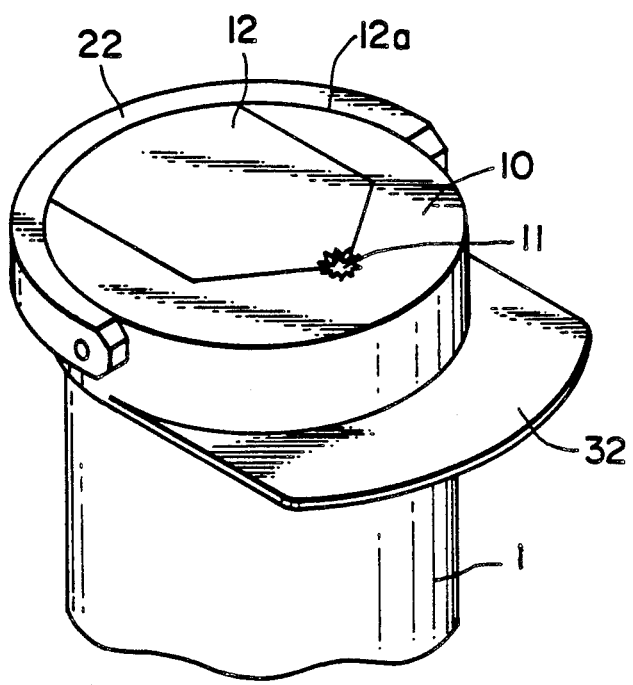
FIGS. 19 and 20 are perspective views respectively illustrating how needle detachers constructed as fourth and fifth embodiments of the present invention are manipulated.

FIG. 19 illustrates the fourth embodiment of the present invention, particularly a situation in which the inner lid 12 is locked along its rear surface 12a by the band 22 provided separately of the protective cover 32 so as to seal the needle trap opening 11 with the inner lid 12.

Figure 20A:
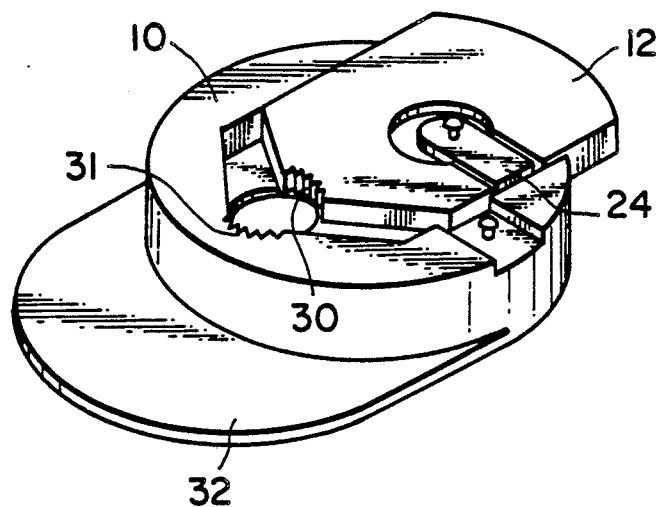
Figure 20B:
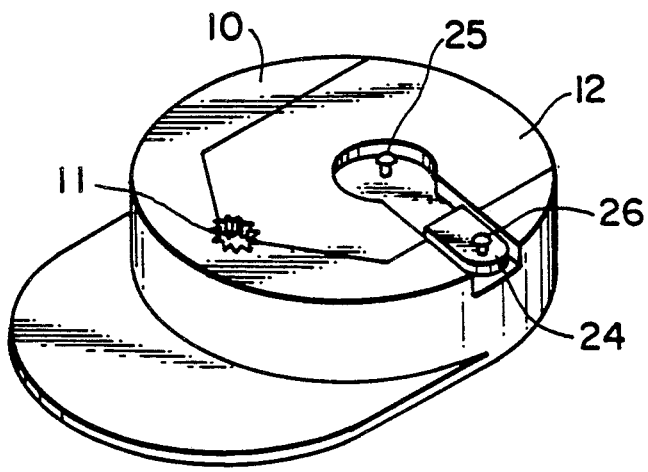
Figure 21A:
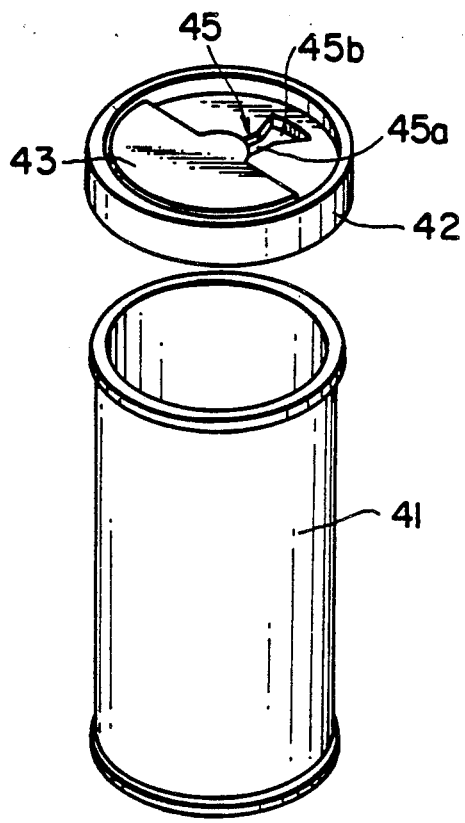
FIGS. 21(A), (B) and (C) are perspective views illustrating the needle detacher of prior art as being expanded, used and closed, respectively.
Figure 21B:
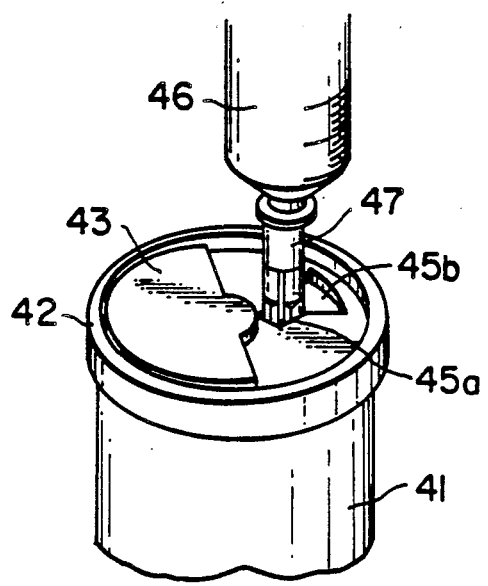
Figure 21C:
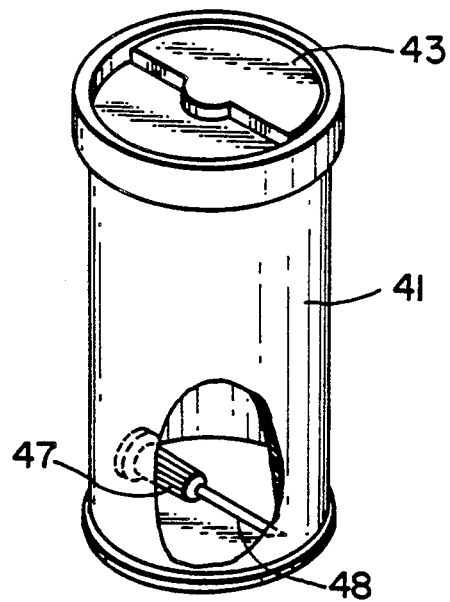

FIG. 20 illustrates the fifth embodiment of the present invention in accordance with which the inner lid 12 is provided on its lateral portion with the foldable band 24 in contrast with the case of the previous third embodiment. FIG. 20(A) and FIG. 20(B) illustrate this embodiment as before and after sealing of the needle trap opening 11, respectively.

As will be readily apparent from the foregoing description, the needle detacher for syringe constructed in accordance with the present invention realizes a significant improvement over the prior art in that, after an adequate number of the needles having been detached from the syringes and received in the container main body, the inner lid may be locked by suitable stop means such as the pin and the band to cover the needle trap opening with the inner lid and then the entire the container thus effectively sealed may be safely thrown away. In this manner, it is assured that the container is maintained in its sealed condition even during transport thereof without a danger that any one of the needles contained within the container might be exposed to the exterior or discharged therefrom and cause an injury.

The present invention provides another advantage that the inner lid can be easily opened and closed since the inner lid is retracted under the action of the associated spring upon release of a hold on the inner lid after the inner lid has been manually pushed forward.

The present invention is advantageous over the prior art also in that the needle neck is firmly held by the inner lid 12 cooperating with the outer lid 10 so as to allow stable and smooth detachment of the needle from the syringe cylinder and that the container main body can be easily sealed because such sealing effect can be maintained only by the stop means for the inner lid.

Furthermore, the protective cover radially extending from the periphery of the outer lid effectively protects the user's finger against a danger that the needle point might accidentally pierce the finger skin and cause an infectious accident when the needle has been contaminated with any pathogenic bacteria or viruses.

Finally, it should be understood that, while the respective embodiments of the present invention have been described as the outer lid 10 is secured to the container main body 1, these two components may be constructed integrally with each other.

While the invention has been particularly shown and described with reference to preferred embodiments thereof, it will be understood by those skilled in the art that various changes in form and details can be made therein without departure from the spirit and scope of the invention.

What is claimed is:

1. A needle detacher for detaching a needle from a syringe cylinder comprising:
   (1) a relatively rigid and elongated container body having an end thereof closed and being configured such that the container body may be firmly grasped by a hand of a user and without substantial deformation of the container body;
   (2) a lid assembly, connected to an other end of said container body, having a stationary outer lid and a movable inner lid which is slidable in relation to the outer lid;
   (3) spring means associated with said inner lid so as to bias the inner lid such that inner lid portions and outer lid portions are spaced apart and define therebetween an adjustable needle trap opening, and wherein said inner lid is manually movable relative to said outer lid that:
      (i) the trap opening may be decreased sufficiently by manual force on the inner lid against said spring means so as to forcibly engage a needle neck of a needle disposed in the trap opening between the said lid portions that a syringe cylinder attached to the needle and the lid assembly may be rotated relative to each other sufficiently to detach the needle from the syringe cylinder; and
      (ii) the trap opening may be increased sufficiently by release of said manual force on said inner lid and by action of said spring so as to release the needle neck from between the said lid portions and allow the needle to fall through said needle chute opening into the container body; and
   (4) closing means associated with the inner lid such that said trap opening is at least substantially closable after said needle has been received in the container body.

2. A needle detacher for syringe as recited in claim 1, wherein there is provided disengageable stop means for the inner lid so as to close the needle trap opening by the inner lid against the action of said spring.

3. A needle detacher for syringe as recited in claim 2, wherein said spring is provided between the inner lid and the outer lid and comprises a bow-shaped, ring-shaped, coil-shaped or cantilever-shaped spring.

4. A needle detacher for syringe as recited in claim 2 or 3, wherein the stop means for the inner lid comprises a ring-shaped member adapted to be reversible with respect to the outer lid and to lock the inner lid against further backward movement so as to close the needle trap opening.

5. A needle detacher for syringe as recited in claim 2 or 3, wherein the stop means for the inner lid comprises a foldable band adapted to be anchored on a pin projecting from the outer lid.

6. A needle detacher for syringe as recited in any one of claims 1, 2 or 3, wherein the needle trap opening includes a rectangular opening formed in the outer lid so that the needle neck engaged with said rectangular opening may be firmly held between said rectangular opening and the inner lid.

7. A needle detacher for syringe as recited in claim 6, wherein there is provided in association with the outer lid a spring adapted to thrust the needle neck out from the rectangular opening when the inner lid is released from the needle neck.

8. A needle detacher for syringe as recited in any one of claims 1, 2 or 3, wherein the needle trap opening comprises a rectangular opening formed in the inner lid so that the needle neck engaged with this rectangular opening is held between the rectangular opening and the outer lid.

9. A needle detacher for syringe as recited in claim 8, wherein the needle neck held in the rectangular opening is thrusted by a wall end of a top plate towards the needle chute opening, as the inner lid is retracted.

10. A needle detacher for syringe as recited in any one of claims 1, 2 or 3, wherein the needle trap opening comprises a recess formed in the outer lid and a recess formed in the inner lid.

11. A needle detacher for syringe as recited in claim 10, wherein said recesses have saw-teeth-like inner walls.

12. A needle detacher for syringe as recited in claim 10, wherein the needle neck held by the recess formed in the inner lid is thrusted by the wall end of the top plate out of said recess towards the needle chute opening, as the inner lid is retracted.

13. A needle detacher for syringe as recited in claim 1, wherein there is provided a protective cover radially extending from the periphery of the outer lid to protect the user's finger against the needle point.

14. A needle detacher for syringe as recited in claim 1, wherein the container main body and the outer lid are constructed integrally with each other.

* * * * *